(12) United States Patent
Herbst et al.

(10) Patent No.: US 6,528,556 B1
(45) Date of Patent: Mar. 4, 2003

(54) PROCESS FOR THE BIOCIDAL FINISHING OF PLASTIC MATERIALS

(75) Inventors: Heinz Herbst, Lörrach (DE); Nadi Ergenc, Therwil (CH); Wolfgang Voigt, Lörrach (DE)

(73) Assignee: Ciba Speciality Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/573,928

(22) Filed: May 18, 2000

(30) Foreign Application Priority Data

Jun. 1, 1999 (CH) ............................................. 1029/99

(51) Int. Cl.⁷ ................................................ C08K 5/00
(52) U.S. Cl. ........................................ 523/122; 524/100
(58) Field of Search ............................ 523/122; 524/100

(56) References Cited

U.S. PATENT DOCUMENTS

| 2,909,420 A | * | 10/1959 | Gysin et al. |
| 4,260,753 A | | 4/1981 | Berrer et al. ................ 544/208 |
| 5,118,346 A | | 6/1992 | Wehner et al. ............. 106/18.3 |

FOREIGN PATENT DOCUMENTS

| CA | 2082533 | | 5/1993 |
| DE | 1914014 | | 10/1969 |
| DE | 149302 | | 7/1981 |
| EP | 0332578 A | * | 9/1989 |
| EP | 0542078 A | * | 5/1993 |

OTHER PUBLICATIONS

Derwent Abstr. 1967–07663H [00] for DE 1914014 (1969).
Derwent Abstr. 1981–71816D [40] for DD 149302 (1981).

* cited by examiner

*Primary Examiner*—Margaret Medley
(74) *Attorney, Agent, or Firm*—Kevin T. Mansfield

(57) ABSTRACT

A process for biocidally finishing plastic materials selected from the group consisting of polyolefin, polystyrene, a halogen-containing polymer, polyacrylate or polymethacrylate, a polymer derived from unsaturated alcohols and amines or from their acyl derivatives or acetals, a homo- or copolymer of cyclic ethers, polyacetal, polyphenylene oxide or polyphenylene sulfide, polyurethane, polyamide or copolyamide, saturated or unsaturated polyester, polycarbonate, a phenol-formaldehyde resin, an epoxy resin or an aminoplastic resin, which process comprises adding a) either during the processing of the plastic materials or, b) in the case of plastic materials prepared via a radical polymerisation, already during the polymerisation or during the processing or, c) in the case of duroplasts prepared from a phenol-formaldehyde resin, epoxy resin or an aminoplastic resin, during the crosslinking reaction, at least one compound selected from the group consisting of 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-tert-butylamino-s-triazine and 2-methylthio-4-ethylamino-6-($\alpha,\beta$-dimethylpropylamino)-s-triazine.

16 Claims, No Drawings

PROCESS FOR THE BIOCIDAL FINISHING OF PLASTIC MATERIALS

The present invention relates to a process for inhibiting the growth of photosynthetically active organisms on the surface of plastic materials, to biocidal polymer compositions, to the use of selected triazine compounds for the biocidal finishing of polymers and to plastic articles produced therefrom.

2-Alkylthio-4,6-diamino-s-triazines are known, inter alia, from DT-OS No. 1 914 014 as selective agents for controlling weeds and grass weeds.

EP-A-0 003 749 discloses selected 2-alkythio-4,6-diamino-s-triazines as effective marine algaecides.

The use of biocidally effective compounds, such as 2,4-bis(ethylamino)-6-chloro-s-triazine or N'-(3,4-dichlorophenyl)-N,N-dimethylurea in polyethylene (PE) or polyvinyl chloride (PVC) is also known and is described, inter alia, in DD 149 302.

If biocidally effective compounds are to be used with long-term effect in plastics, they must meet other requirements besides their biological activity, originating from the processing (temperature and shear forces) as well as from the use of the plastics (outdoor or indoor use).

The compounds proposed in the present state of the art are not able to be fully satisfactory in this respect so that there is still a need for having further bioactive compounds available which have a high biological effectivity and which meet the specific requirements for plastics.

Surprisingly, it has now been found that selected methylthio-s-triazines have excellent compatibility with polymers, do not sweat even after a prolonged period of time and have superior thermal resistance during their incorporation into the polymers as well as during the use of the plastic articles prepared therefrom.

The biocidal effect is maintained even after prolonged outdoor use and is virtually unaffected by wetness and moisture so that plastic articles finished in this manner are also suitable for uses in which they are temporarily or permanently surrounded by water or humidity. They are even suitable in an unusually advantageous manner for all those material applications in which the material is in contact with water over an extended period of time or permanently.

Within the scope of this invention, the term biocidal effect shall be taken to mean mainly a herbicidal effect, i.e. an inhibition of the growth of photosynthetically active organisms, in particular algae and mosses.

In one of its aspects, this invention relates to a process for biocidally finishing plastic materials selected from the group consisting of polyolefin, polystyrene, a halogen-containing polymer, polyacrylate or polymethacrylate, a polymer derived from unsaturated alcohols and amines or from their acyl derivatives or acetals, a homo- or copolymer of cyclic ethers, polyacetal, polyphenylene oxide or polyphenylene sulfide, polyurethane, polyamide or copolyamide, saturated or unsaturated polyester, polycarbonate, a phenol-formaldehyde resin, an epoxy resin or an aminoplastic resin, which process comprises adding a) either during the processing of the plastic materials or,
b) in the case of plastic materials prepared via a radical polymerisation, already during the polymerisation or during the processing or,
c) in the case of duroplasts prepared from a phenol-formaldehyde resin, epoxy resin or an aminoplastic resin, during the crosslinking reaction, at least one compound selected from the group consisting of 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-tert-butylamino-s-triazine and 2-methylthio-4-ethylamino-6-($\alpha,\beta$-dimethylpropylamino)-s-triazine.

The use of 2-methylthio-4-cyclopropylamino-6-tert-butylamino-s-triazine and/or of 2-methylthio-4-ethylamino-6-tert-butylamino-s-triazine is particularly preferred.

The compounds as such are known and are described, inter alia, in EP-A-0 003 749.

The biocidally effective compound is preferably added in an amount from 0.01 to 10% by weight, particularly preferably from 0.02 to 5% by weight and, very particularly preferably, from 0.05% to 3% by weight, based on the plastic material.

The biocidally effective compound can be added as pure substance or as a mixture with other plastic materials (master batch), such as LDPE, HDPE, PP or PET.

Selected plastic materials suitable for the process are mentioned above and are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/ propylene copolymers, linear low density polyethylene (LLDPE) and mixtures thereof with low density polyethylene (LDPE), propylene/but-1-ene copolymers, propylene/ isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/ isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ ethylene-acrylic acid copolymers (EM), LLDPE/EVA, LLDPE/EAA and alternating or random polyalkylene/ carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/ butadiene/alkyl acrylate, styrene/butadiene/alkyl methacrylate, styrene/maleic anhydride, styrene/ acrylonitrile/methyl acrylate; mixtures of high impact strength of styrene copolymers and another polymer, for example a polyacrylate, a diene polymer or an ethylene/ propylene/diene terpolymer; and block copolymers of styrene such as styrene/butadiene/styrene, styrene/isoprene/ styrene, styrene/ethylene/butylene/styrene or styrene/ ethylene/propylene/ styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/ propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/ alkyl acrylate copolymers, acrylonitrile/alkoxyalkyl acrylate or acrylonitrile/vinyl halide copolymers or acrylonitrile/ alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

18. Polycarbonates and polyester carbonates.

19. Crosslinked polymers derived from aldehydes on the one hand and from phenols, ureas or melamines on the other hand, such as phenol-formaldehyde, urea-formaldehyde and melamine-formaldehyde resins.

20. Unsaturated polyesters are derived from anhydrides or acids of aromatic, saturated and unsaturated aliphatic dicarboxylic acids and from aromatic, saturated and unsaturated aliphatic diols such as fumaric acid, maleic acid, maleic anhydride, phthalic anhydride, isophthalic anhydride, terephthalic acid, adipic acid, ethylene glycol, propanediol, butanediol, neopentyl glycol, bisphenol A, bisphenol F, butenediol, etc. Curing of the unsaturated polyesters is carried out radically in a crosslinking copolymerisation with vinyl monomers such as styrene, p-methylstyrene, $\alpha$-methylstyrene, methyl methacrylate, acrylic acid, methyl acrylate, acrylonitrile, and mixtures of these monomers.

21. Epoxy resins are derived from di- and polyfunctional epoxides which are crosslinked with polyamines, such as diethylenetriamine, triethylenetetramine, tetraethylenepentamine, methylenedianiline, diaminodiphenylsulfone and polyaminoamides or with dicarboxylic acids and their anhydrides, such as hexahydrophthalic anhydride, phthalic anhydride, pyromellitic anhydride, methylnadic anhydride.

Preferred plastic materials are thermoplastics.

Preferred duroplasts are crosslinked epoxy resins, unsaturated polyesters and the phenolformaldehyde, urea-formaldehyde and melamine-formaldehyde resins.

Preferred plastic materials are polyethylene, polypropylene, polyisobutylene, polyvinyl chloride, polycarbonate, polyacrylate, polymethacrylate, polyamide 6, polyamide 6.6 or copolyamide, polyethylene therephthalate, polybutylene terephthalate, an unsaturated polyester resin (UP resin), an epoxy resin, a phenol-formaldehyde resin or a melamine resin.

Particularly preferred are polyethylene, polypropylene, polyvinyl chloride, polycarbonate, polyacrylate, polymethacrylate, polyethylene therephthalate, an unsaturated polyester resin, an epoxy resin, a phenol-formaldehyde resin or a melamine resin.

Very particularly preferred are LDPE, HDPE, polypropylene, polyethylene terephthalate, UP resin or polymethacrylates.

In principle, the biocidally effective compound can already be added during the preparation of the polymers if it does not interfere with the preparation process.

An advantageous processing measure taken when preparing polyacrylate or polymethacrylate and crosslinked polyether resins is to add the biocidally effective compound already during the polymerisation of acrylate or methacrylate or during the crosslinking of the unsaturated polyester resins.

When preparing duroplasts from epoxy resins, phenol-formaldehyde resins and melamine resins it is also advantageous to add the biocidally effective compound already during the crosslinking reaction.

Other biocides may be added besides the above-mentioned biocidally effective compounds.

In practice, active substances are often used in combination with other biocides. Thus it is possible to use the compounds in combination with $Cu_2O$, CuSCN, zinc oxide, triorganotin compounds, for example tributyltin fluoride or triphenyltin chloride, metallic copper or triazines or in general with those compounds known to the skilled person to be effective against animal or vegetable fouling. The person skilled in the art will find suitable compounds e.g. in "The Pesticide Manual", editor: British Crop Protection Council, 1997.

Examples of such additional biocides are:
a) Organosulfur compounds, e.g. methylenedithiocyanate (MBT), isothiazolones or 3,5-dimethyltetrahydro-1,3,5-2H-thiodiazine-2-thione (DMTT).
b) Chlorinated phenols, for example sodium pentachlorophenolate, 2,4,4'-trichloro-2-hydroxydiphenyl ether or 4,4'-dichloro-2-hydroxydiphenyl ether. Such compounds are distinguished by having a very broad spectrum of activity.
c) Copper salts, for example copper sulfate and copper nitrate as additional algaecides.
d) Triazines, for example 2-methylthio-4-tert-butylamino-6-cyclopropylamino-s-triazine, in particular as algaecides.
e) Triorganotin compounds, for example bis-tributyltin oxide (TBTO), in particular as fungicides and algaecides.
f) Bactericides, for examples silver salts, 2.3.5.6-tetrachloro-4(methylsulfonyl)pyridine, 4,5-dichloro-2-n-octyl-4-isothiazolin-3-one, N-butylbenzisothiazoline, 10.10'-oxybisphenoxyarsine, zinc-2-pyridinethiol-1-oxide or zinc oxide.

Besides other biocides, the plastic material may also contain one or more than one component from the group consisting of pigments, dyes, fillers, adhesion promoters, antioxidants and light stabilisers.

The pigments are, for example, carbon black, graphite, titanium dioxide, iron oxide, aluminium bronze, phthalocyanines or organic coloured pigments as well as their blends with inorganic pigments.

Examples of fillers are talcum, aluminium oxide, aluminium silicate, baryte, mica, glass fibres, glass beads or silicium dioxide.

The biocidally effective compounds can also be applied to a substrate (e.g. zeolite) and can be incorporated together with it.

The plastic material preferably contains additional processing stabilisers and/or light stabilisers. Examples are given below.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'- methylenebis[6-(α,α-dimethylbenzyl)-4-nonylphenol], 4,4'-methylenebis-(2,6-di-tert-butylphenol), 4,4'-methylenebis (6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl) malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tertoctyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, N,N-bis(2,2,6,6-tetra-methyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl )-2'-hydroxyphenyl]-2H-benzotriazole with polyethylene glycol 300; [R—CH$_2$CH$_2$—COO—CH$_2$—]—$_2$, where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl] benzotriazole.

2.2. 2-Hydroxbenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-di-chloro-1,3,5-triazine, tris(2,2,6,6-tetramethyl-4-piperidyl) nitrilotriacetate, tetrakis(2,2,6,6-tetramethyl-4-piperidyl)-1, 2,3,4-butanetetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4, 6-trichloro-1,3,5-triazine as well as 4-butylamino-2,2,6,6-tetramethylpiperidine (CAS Reg. No. [136504-96-6]); N-(2, 2,6,6-tetramethyl-4-piperidyl)-n-dodecylsuccinimide, N-(1, 2,2,6,6-pentamethyl-4-piperidyl)-n-dodecylsuccinimide, 2-undecyl-7,7,9,9-tetramethyl-1-oxa-3,8-diaza-4-oxo-spiro-[4,5]decane, a reaction product of 7,7,9,9-tetramethyl-2-cycloundecyl-1-oxa-3,8-diaza-4-oxospiro [4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of -4-methoxy-methylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tertbutoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethyphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butyl-phenyl) 4,4'-biphenylene diphosphonite, 6-isooctyloxy-2,4,8,10-tetra-tert-butyl-12H-dibenz-[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-di-benz[d,g]-1,3,2-dioxaphosphocin, 2,2',2''-nitrilo[triethyltris(3,3',5,5'-tetra-tert-butyl-1,1'-biphenyl-2,2'-diyl)phosphite], 2-ethylhexyl (3,3', 5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Especially preferred are the following phosphites:

Tris(2,4-di-tert-butylphenyl) phosphite (Irgafos®168, Ciba-Geigy), tris(nonylphenyl) phosphite, (A)

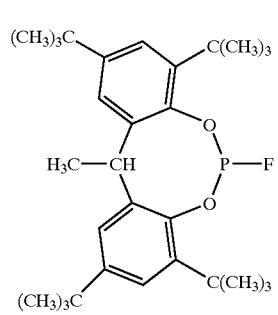

(B)

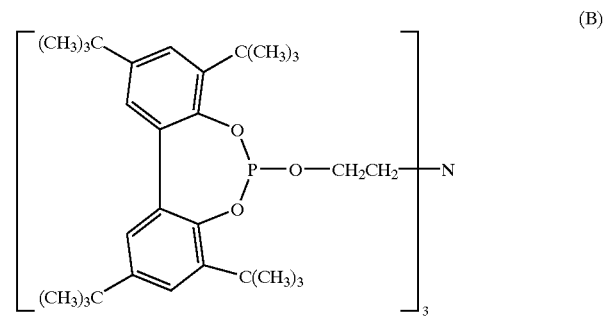

(C)

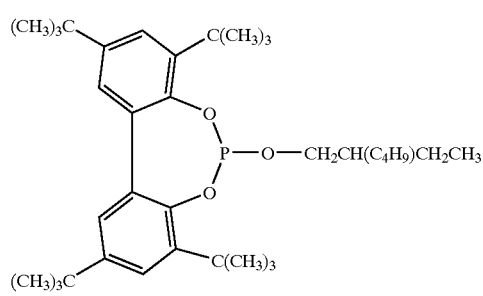

(D)

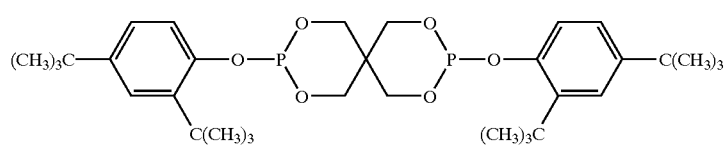

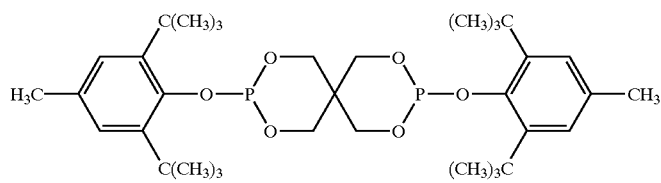

(E)

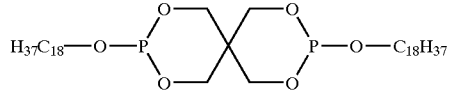

(F)

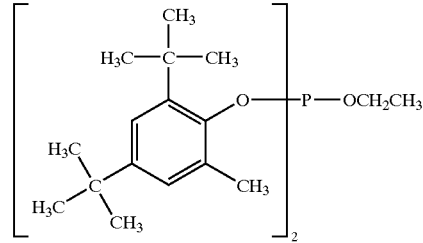

(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methyinitrone, N-octyl-alpha-heptylnitrone, N-lauryl-alpha-undecyinitrone, N-tetradecyl-alpha-tridecyinitrone, N-hexadecyl-alpha-pentadecyinitrone, N-octadecyl-alpha-heptadecylnitrone, N-hexadecyl-alpha-heptadecylnitrone, N-ocatadecyl-alpha-pentadecyinitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibres of other natural products, synthetic fibres.

13. Other additives, for example, plasticisers, lubricants, emulsifiers, pigments, rheology additives, catalysts, flow control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butylbenzofuran-2-one, 5,7-di-tert-butyl-3-[-4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butyl-benzofuran-2-one.

The process can be carried out in any temperature-controllable vessel which is fitted with a stirring device. These vessels may be, for example, closed apparatus, such as kneaders, mixers or mixing vessels. The process can also be carried out in an extruder or kneading machine. It is irrelevant whether processing is carried out in an inert gas atmosphere or in the presence of atmospheric oxygen.

Thermoplastic polymers are usually molten during processing and the biocide is equally distributed during processing. The temperature during processing depends on the thermoplastic polymer and is usually in the range between 150° C. to 280° C.

In the case of thermosetting polymers, the biocide is usually added to the resin before the thermosetting step. Crosslinking is typically carried out at a temperature between 50° C. to 150° C.

It is also possible to carry out the process in several steps, for example a) 1) premixture, 2) reaction/moulding in a temperature-controllable vessel/mould
b) 1) premixture, 2) application to the article, 3) reaction/moulding in a temperature-controllable chamber.

The end products can be prepared by blowing processes (films), extrusion, thermoforming or casting processes, injection moulding, rotomoulding.

Examples of individual plastic materials and of the end products which may be prepared therefrom are given below:

LDPE films, greenhouse applications, tubes, irrigation applications, inliners;

HDPE films, tubes, injection moulding applications, rotomoulding applications, artificial wood, bank stabilisation systems, boats, gang boards, inliners;

MDPE tubes, rotomoulding applications, irrigation applications; polyisobutylene roofing, flat roofs, tubes;

PC greenhouse applications, roof applications;

PET greenhouse applications, roof applications, fabrics;

PP artificial lawn, buoys, garden application, fabrics;

UP (unsaturated polyester resin) boats, whirlpool, pool, bathtub, bath applications, sanitary applications, camping, caravan, mobile home, garden application, gel coat, laminate;

epoxy resins boats, whirlpool, pool, bathtub, bath applications, sanitary applications, camping, caravan, mobile home, garden application, gel coat, laminate, kitchen applications;

PVC inliners, sidings, flat roofs, tents;

acrylates (in particular PMMA) whirlpool, bathtub, bath applications, sanitary applications, laminate, kitchen applications;

phenol-formaldehyde resins whirlpool, bathtub, bath applications, sanitary applications, laminate;

aminoplasts (in particular melamine resins) whirlpool, bathtub, bath applications, sanitary applications, laminate;

polyamides (PA6, PA6.6) carpet, fibre application, camping.

Blends of these plastic materials and articles produced therefrom are also possible.

This invention also relates to a composition, which comprises a plastic material selected from the group consisting of polyolefin, polystyrene, a halogen-containing polymer, polyacrylate or polymethacrylate, a polymer which is derived from unsaturated alcohols and amines or from their acyl derivatives or acetals, a homo- or copolymer of cyclic ethers, polyacetal, polyphenylene oxide or polyphenylene sulfide, polyurethane, polyamide or copolyamide, saturated or unsaturated polyester, polycarbonate, a phenol-formaldehyde resin, an epoxy resin or an aminoplastic resin, and a biocidally effective compound from the group consisting of 2-methylthio-4-cyclopropylamino-6-($\alpha,\beta$-dimethylpropylamino)-s-triazine, 2-methylthio-4-cyclopropylamino-6-tertbutylamino-s-triazine, 2-methylthio-4-ethylamino-6-tert-butylamino-s-triazine and 2-methylthio-4-ethylamino-6-($\alpha$, $\beta$-dimethylpropylamino)-s-triazine.

Another object of the invention is the use of a compound selected from the group consisting of 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-tert-butylamino-s-triazine and 2-methylthio-4-ethylamino-6-($\alpha,\beta$-dimethylpropylamino)-s-triazine for biocidally finishing polyolefin, polystyrene, a halogen-containing polymer, polyacrylate or polymethacrylate, a polymer which is derived from unsaturated alcohols and amines or from their acyl derivatives or acetals, a homo- or copolymer of cyclic ethers, polyacetal, polyphenylene oxide or polyphenylene sulfide, polyurethane, polyamide or copolyamide, saturated or unsaturated polyester, polycarbonate, a phenol-formaldehyde resin, or an aminoplastic resin.

This invention also relates to plastic articles consisting of a polyolefin, polystyrene, a halogen-containing polymer, polyacrylate or polymethacrylate, a polymer which is derived from unsaturated alcohols and amines or from their acyl derivatives or acetals, a homo- or copolymer of cyclic ethers, polyacetal, polyphenylene oxide or polyphenylene sulfide, polyurethane, polyamide or copolyamide, saturated or unsaturated polyester, polycarbonate, a phenol-formaldehyde resin, an epoxy resin or an aminoplastic resin, comprising 2-methylthio-4-cyclopropylamino-6-($\alpha,\beta$-dimethylpropylamino)-s-triazine, 2-methylthio-4-cyclopropylamino-6-tertbutylamino-s-triazine, 2-methylthio-4-ethylamino-6-tert-butylamino-s-triazine or 2-methylthio-4-ethylamino-6-($\alpha,\beta$-dimethylpropylamino)-s-triazine.

The following Examples illustrate the invention.

EXAMPLE 1–3

Preparation of a Master Batch

2-Methylthio-4-cyclopropylamino-6-tert-butylamino-s-triazine (CAS No. 28159-98-0) is incorporated into a polymer according to Table 1. To this purpose, a mixture consisting of the active substance and the polymer is prepared and this mixture is homogenised for 2 minutes in a mechanical stirring apparatus (Henschel).

The mixture is compounded in an extruder under a nitrogen atmosphere to granules.

These granules may be used for incorporation and further dilution.

TABLE 1

| Example | [%] Active substance | Polymer | Compounding |
|---|---|---|---|
| 1 | 10 | LDPE (Escorene ® LD 100BW) | 220° C. |
| 2 | 25 | PET-G (Eastar ® 6763) | 180° C. |
| 3 | 25 | PEBA (Pebax ® 2533) | 180° C. |

Incorporation Examples

EXAMPLES 4–12

2-Methylthio-4-cyclopropylamino-6-tert-butylamino-s-triazine (A) is incorporated as a pure substance or in the form of a masterbatch (Table 1) into a polymer (Table 2). To this purpose, a mixture consisting of the active substance and the polymer is prepared and this mixture is homogenised for 2 minutes in a mechanical stirring apparatus (Henschel). The mixture is compounded in an extruder under a nitrogen atmosphere to granules.

These granules are then moulded into sheets.

TABLE 2

| Example | Active substance | Polymer | Compounding |
|---|---|---|---|
| 4 | 0% (A) | PP Profax ® 6501 | injection moulding max. 230° C. |
| 5 | 0.2% (A) | PP Profax ® 6501 | injection moulding max. 230° C. |
| 6 | 0% (A) | PMMA Plexiglas ® 6N | injection moulding max. 230° C. |
| 7 | 0.5% (A) | PMMA Plexiglas ® 6N | injection moulding max. 230° C. |
| 8 | 1.0% (A) | PMMA Plexiglas ® 6N | injection moulding max. 230° C. |

TABLE 2-continued

| Example | Active substance | Polymer | Compounding |
|---|---|---|---|
| 9 | 0% (A) | PVC Evipol ® SH 7020 | rolled sheet max. 160° C. |
| 10 | 0.10% (A) | PVC Evipol ® SH 7020 | rolled sheet max. 160° C. |
| 11 | 0% | HDPE MS 6591 | injection moulding max. 230° C. |
| 12 | 0.10% (A) | HDPE MS 6591 | injection moulding max. 230° C. |

EXAMPLES 13–14

2-Methylthio-4-cyclopropylamino-6-tert-butylamino-s-triazine (A) is mixed as a pure substance with the monomers and is polymerised into some form.

| Example | Active substance | Polymer |
|---|---|---|
| 13 | 0 | UP* Palatal ® P4 |
| 14 | 0.5% (A) | UP Palatal ® P4 |

*unsaturated polyester

C) Biological Effectivity

Agar sheets are incubated for 7 days with a unicellular algae culture (Pseudokirchneriella subcapitata strain No. 61.81 SAG). The test samples are then placed on the agar sheets. The growth of the algae is evaluated after 7 days.

Strong inhibition is found in the case of the mixtures of this invention, which shows in the formation of an inhibiting areola (mm).

TABLE 3

| Example | Inhibiting areola [mm] | Example | Inhibiting areola [mm] |
|---|---|---|---|
| 4 | 0 | | |
| 5 | 8 | 10 | 30 |
| 6 | 0 | 11 | 0 |
| 7 | 20 | 12 | 30 |
| 8 | 25 | 13 | 0 |
| 9 | 0 | 14 | 6 |

What is claimed is:

1. A process for the biocidal finishing of plastic materials selected from the group consisting of polyethylene, polypropylene, polyvinyl chloride, polyacrylate, polymethacrylate, polyethylene terephthalate, unsaturated polyesters, polycarbonate, phenol-formaldehyde resins, epoxy resins and melamine resins, which process comprises adding
    a) either during the processing of the plastic materials or,
    b) in the case of plastic materials prepared via a radical polymerisation, already during the polymerisation or during the processing or,
    c) in the case of duroplasts prepared from a phenol-formaldehyde resin, epoxy resin or a melamine resin, during the crosslinking reaction,
    a biocidally effective amount of at least one compound selected from the group consisting of 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-tert-butylamino-s-triazine and 2-methylthio-4-ethylamino-6-($\alpha,\beta$-dimethylpropylamino)-s-triazine.

2. A process according to claim 1, wherein the biocidally effective compound is selected from the group consisting of 2-methylthio-4-cyclopropylamino-6-tert-butylamino-s-triazine, 2-methylthio-4-ethylamino-6-tert-butylamino-s-triazine and mixtures thereof.

3. A process according to claim 1, which comprises adding the biocidally effective compound in an amount from 0.01 to 10% by weight, based on the plastic material.

4. A plastic article consisting of polyethylene, polypropylene, polyvinyl chloride, polyacrylate, polymethacrylate, polyethylene terephthalate, an unsaturated polyester, polycarbonate, a phenol-formaldehyde resin, an epoxy resin or a melamine resin, and a biocidally effective amount of 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-tert-butylamino-s-triazine or 2-methylthio-4-ethylamino-6-($\alpha,\beta$-dimethylpropylamino)-s-triazine.

5. A plastic article according to claim 4, wherein the biocidally effective compound is 2-methylthio-4-ethylamino-6-($\alpha,\beta$-dimethylpropylamino)-s-triazine.

6. A process according to claim 1, wherein the plastic material is selected from the group consisting of low density polyethylene, high density polyethylene, polypropylene, polyethylene terephthalate, unsaturated polyester resins and polymethacrylate.

7. A process according to claim 1, which comprises adding the biocidally effective compound already during the polymerisation of acrylate or methacrylate or during the crosslinking of the unsaturated polyester resins.

8. A process according to claim 1, wherein the plastic material comprises further additional processing stabilisers and/or light stabilisers.

9. A composition, which comprises a plastic material selected from the group consisting of polyethylene, polypropylene, polyvinyl chloride, polycarbonate, polyacrylate, polymethacrylate, polyethylene terephthalate, unsaturated polyesters, polycarbonate, phenol-formaldehyde resins, epoxy resins and melamine resins, and a biocidally effective amount of a compound selected from the group consisting of 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-tert-butylamino-s-triazine and 2-methylthio-4-ethylamino-6-($\alpha,\beta$-dimethylpropylamino)-s-triazine.

10. A plastic article according to claim 4, wherein the biocidally effective compound is 2-methylthio-4-ethylamino-6-tert-butylamino-s-triazine.

11. A composition according to claim 9, wherein the biocidally effective compound is 2-methylthio-4-cyclopropylamino-6-($\alpha,\beta$-dimethylpropylamino)-s-triazine.

12. A composition according to claim 9, wherein the biocidally effective compound is 2-methylthio-4-cyclopropylamino-6-tert-butylamino-s-triazine.

13. A composition according to claim 9, wherein the biocidally effective compound is 2-methylthio-4-ethylamino-6-tert-butylamino-s-triazine.

14. A composition according to claim 9, wherein the biocidally effective compound is 2-methylthio-4-ethylamino-6-($\alpha,\beta$-dimethylpropylamino)-s-triazine.

15. A plastic article according to claim 4, wherein the biocidally effective compound is 2-methylthio-4-cyclopropylamino-6-($\alpha,\beta$-dimethylpropylamino)-s-triazine.

16. A plastic article according to claim 4, wherein the biocidally effective compound is 2-methylthio-4-cyclopropylamino-6-tert-butylamino-s-triazine.

* * * * *